United States Patent [19]

Milam

[11] 4,235,825

[45] Nov. 25, 1980

[54] PRODUCTION OF DICHLOROBENZENE

[75] Inventor: Joseph E. Milam, New Martinsville, W. Va.

[73] Assignee: PPG Industries, Inc., Pittsburgh, Pa.

[21] Appl. No.: 90,841

[22] Filed: Nov. 2, 1979

[51] Int. Cl.³ .............................................. C07C 25/04
[52] U.S. Cl. ..................................................... 370/210
[58] Field of Search .................................... 260/650 R

[56] References Cited

U.S. PATENT DOCUMENTS

| | | | |
|---|---|---|---|
| 3,029,296 | 4/1962 | White et al. | 260/650 R |
| 3,636,171 | 1/1972 | Krumel et al. | 260/650 R |
| 4,017,551 | 4/1977 | Milam et al. | 260/650 R |
| 4,166,075 | 8/1979 | Blumenfield et al. | 260/650 R |

FOREIGN PATENT DOCUMENTS 223024  6/1957  Australia .

*Primary Examiner*—Curtis R. Davis
*Attorney, Agent, or Firm*—Edward J. Whitfield

[57] ABSTRACT

Dichlorobenzene having a higher ratio of para isomer to ortho isomer is produced by the liquid phase chlorination of benzene or monochlorobenzene in the presence of a two-component catalyst consisting of a metal halide, e.g., ferric chloride, and diethylether.

4 Claims, No Drawings

PRODUCTION OF DICHLOROBENZENE

BACKGROUND OF THE INVENTION

It is known to produce isomeric mixtures of dichlorobenzene by contacting gaseous chlorine with benzene or monochlorobenzene in the liquid phase in the presence of a metal halide catalyst, e.g., ferric chloride, aluminum chloride, antimony chloride and the like. However, in this process, the maximum molar ratio or para-dichlorobenzene isomer to orthodichlorobenzene isomer is only about 1.5 to 1. Since the para-dichlorobenzene isomer is the more valuable product it is desirable to increase the proportion of para- to ortho isomer.

In order to effect this desirable increase in proportion of para- to ortho isomers in the product dichlorobenzene, the prior art has employed elemental sulfur or sulfur-containing compounds as co-catalysts along with the metal halide as described, for example, in U.S. Pat. No. 3,226,447 and Australian Pat. No. 223,024. Since, however, hydrochloric acid is often recovered as a salable by-product, care must be taken to avoid sulfur contamination of the hydrochloric acid as well as sulfur contamination of the product dichlorobenzene.

DESCRIPTION OF THE INVENTION

In accordance with this invention dichlorobenzene having an increased molar ratio of para isomer to ortho isomer is prepared by the chlorination of benzene or monochlorobenzene in the liquid phase in the presence of a two-component catalyst consisting of a conventional metal halide chlorination catalyst and diethylether.

Any conventional metal halide chlorination catalyst may be used in combination with diethylether in accordance with this invention, for example, ferric chloride, aluminum chloride, antimony chloride and the like, ferric chloride being preferred. The amount of metal halide catalyst may vary over a wide range, for example from about 0.1 to about 10 percent or more by weight of metal halide catalyst based on weight of benzene or monochlorobenzene, although satisfactory results typically obtain at a metal halide catalyst concentration of from about 1 to about 5 weight percent. Likewise the amount of diethylether may vary considerably, for example, from about 0.1 to about 5 percent or more by weight based on weight of benzene or monochlorobenzene, with satisfactory results obtaining at a diethylether concentration of from about 0.5 to about 3 weight percent.

The reaction is conducted in known fashion by contacting a liquid mixture of benzene or monochlorobenzene and the two-component catalyst with gaseous chlorine typically in stoichiometric amount, preferably in the absence of light and at a temperature typically in the range of 0° C. to 100° C., preferably from about 20° C. to about 70° C., at a pressure sufficient to maintain the liquid phase; the reaction preferably being conducted at atmospheric pressure.

The invention is further illustrated but is not limited to be limited by the following Examples.

EXAMPLE 1

The reaction vessel was a one liter, four-necked, round bottom flask provided with a water cooled condenser, stirring means, a thermometer, chlorine injection and sample withdrawal means. The flask was painted black to exclude light and was immersed in a water bath to maintain the reaction temperature constant. To the flask was added 500 grams of benzene, 2.5 grams of ferric chloride and 1.14 grams of diethylether. Gaseous chlorine was metered into the reactor at a rate of about 1.7 grams per minute over a period of about 5 hours. During chlorine addition the reactor contents were continuously stirred and maintained at a temperature of 50° C. At the completion of chlorine addition, the reactor was shut-down and the contents withdrawn and analyzed, the results of which analysis are summarized in Table 1.

EXAMPLE 2

The procedure described in Example 1 was followed, except that only 2.5 grams of ferric chloride was used as the catalyst. The results of this experiment are also summarized in Table 1.

TABLE 1

Liquid phase chlorination of benzene using ferric chloride catalyst and ferric chloride plus diethylether catalyst. All results reported in mole percent, unless otherwise indicated.

| Run No. | 1 | 2 |
|---|---|---|
| Catalyst | $FeCl_3/C_2H_5O$ | $FeCl_3$ |
| Benzene | 1.46 | 2.77 |
| Monochlorobenzene | 68.55 | 67.28 |
| m-dichlorobenzene | 0.38 | 0.88 |
| p-dichlorobenzene | 20.74 | 17.06 |
| o-dichlorobenzene | 8.70 | 11.53 |
| Trichlorobenzene | 0.11 | 0.43 |
| Ratio, P/O isomers | 2.38 | 1.49 |

I claim:

1. In a process for producing isomeric mixtures of dichlorobenzene by chlorinating benzene or monochlorobenzene in the liquid phase in the presence of a metal halide catalyst, the improvement wherein the reaction is conducted in the presence of diethylether as co-catalyst to produce dichlorobenzene having a higher ratio of para isomer to ortho isomer than that produced were the reaction conducted in the presence of only metal halide as catalyst.

2. The improvement of claim 1 wherein the metal halide is ferric chloride.

3. The improvement of claim 1 wherein metal halide is present in an amount ranging from 0.01 to 10 percent by weight based on weight of benzene or monochlorobenzene and diethylether is present in amounts ranging from 0.1 to 5 percent by weight based on weight of benzene or monochlorobenzene.

4. The improvement of claim 3 wherein metal halide is present in amounts ranging from 1 to 5 percent by weight and diethylether is present in amounts ranging from 0.5 to 3 percent by weight.

* * * * *